United States Patent
Dewkar et al.

(10) Patent No.: US 6,825,383 B1
(45) Date of Patent: Nov. 30, 2004

(54) CATALYTIC PROCESS FOR REGIOSPECIFIC CHLORINATION OF ALKANES, ALKENES AND ARENES

(75) Inventors: Gajanan Kundalik Dewkar, Maharashtra (IN); Vinay Vijayraj Thakur, Maharashtra (IN); Sanjeevani Amrit Pardhy, Maharashtra (IN); Arumugam Sudalai, Maharashtra (IN); Sukumar Devotta, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/665,411

(22) Filed: Sep. 22, 2003

(51) Int. Cl.$^7$ .......................... C07C 45/00; C07C 33/46; C07C 17/00

(52) U.S. Cl. ....................... 568/323; 568/335; 568/812; 570/190; 570/198

(58) Field of Search ................................ 568/323, 335, 568/812; 570/190, 198

(56) References Cited

U.S. PATENT DOCUMENTS 6,118,018 A * 9/2000 Savidakis et al. ........... 560/103

* cited by examiner

*Primary Examiner*—Samuel Barts
*Assistant Examiner*—Sikarl A. Witherspoon
(74) *Attorney, Agent, or Firm*—Nixon & Vanderhye P.C.

(57) ABSTRACT

The present invention provides a process for regiospecific chlorination of an aromatic or aliphatic compound with a chlorine source comprising a metal chloride and other than $Cl_2$ and $SO_2Cl_2$ in presence of hypervalent iodine catalyst and in acidic medium.

11 Claims, No Drawings

CATALYTIC PROCESS FOR REGIOSPECIFIC CHLORINATION OF ALKANES, ALKENES AND ARENES

FIELD OF THE INVENTION

The present invention relates to a new process for the chlorination of alkanes, alkenes and arenes. More particularly, the present invention relates to a process for chlorination of alkanes, alkenes and arenes using alkali metal chlorides as chlorinating agents in the presence of hypervalent iodine as catalyst. The present invention also relates to a process for the highly regiospecific chlorination of arenes using sodium chloride as a chlorinating agent in the presence of catalytic amount of sodium periodate under acidic medium (pH 2–3).

BACKGROUND OF THE INVENTION

The chlorination of alkanes, alkenes and arenes is a prominent organic reaction with wide laboratory use and industrial application. The introduction of chlorine on to aromatic rings by electrophilic substitution is an important synthetic transformation because chlorinated hydrocarbons are recognized as versatile starting materials and additives in the production of high quality insecticides, fungicides, herbicides, dyes, pharmaceuticals, etc. Since 1940, large quantities of chlorobenzene have been used in the production of DDT, a widely used insecticide. 1,4-Dichlorobenzene is a solid at room temperature its main use is as mothballs and room deodorant blocks. The major use of p-chlorotoluene is in the manufacture of p-chlorobenzotrifluoride, a key intermediate in dinitroaniline and diphenyl ether herbicides p-Chlorotoluene is an intermediate for a class of novel polyketone polymers.

In the prior art, the chlorination of arenes is known to be achieved by several methods. One of the simplest methods of chlorination of activated aromatic compounds consists of stirring the respective activated aromatic compounds such as anisole, phenol, etc. with chlorinating agent such as $Cl_2$ in the absence of added catalyst. Weakly activated or non-activated substrates are generally reacted with chlorine in the presence of Lewis acids such as $FeCl_3$ or $AlCl_3$. [Ref. (1) ge la Mare, P. B. D.; in "*Electrophilic Halogenation*" Cambridge University Press, Cambridge, 1976. (2) Taylor, R.; in "*Electrophilic Aroamtic Substitution*" Wiley, Chichester, 1990, pp 362412.]. A number of other types of chlorine containing compounds such as $PhICl_2$ in $CF_3CO_2H$ (Ref *J. Am. Chem. Soc.* 1960, 82, 5823), alkyl and acyl hypochlorides (Ref *Chem. Rev.* 1954, 54, 925), dichlorine monoxide ($Cl_2O$) (Ref *J. Am. Chem. Soc.* 1982, 104, 4680) and N-chloramines, -amides, -sulfonamides (Ref (1) *J. Chem. Soc. Perkin Trans.* 2 1987, 1533, 1988, 385; 1989, 1529; 1989, 1537. (2) *Synthesis* 1993, 237) have been used to perform ring chlorination of aromatics.

For the chlorination of anisole, $SO_2Cl_2$ was used in the presence of the acidic zeolite such as ZF520 (Ref. *J. Org. Chem.* 1990, 55, 5260). Chlorination of anisole was also carried out using t-butyl hypochlorite in the presence of acidic silica gel (Ref *Synthesis* 1985, 1155). Synthesis of haloarenes was commonly performed with molecular chlorine in the presence of catalysts such as aluminium (III), iron (III), tin (IV) or zinc (II) chlorides.

In the prior art, o-chloroaniline was prepared by reducing 1-chloro-2-nitrobenzene with iron filings and HCl and p-chloroaniline was prepared by reduction of 1-chloro-4-nitrobenzene with iron filings and HCl (Ref *J. Chem. Soc.* 1921, 119, 1013) or from p-chlorobenzoic acid by treatment with hydroxylamine and commercial polyphoshoric acid at 150–170° C. (Ref *J. Am. Chem. Soc.* 1953, 75, 2014) or from 1,4-dichlorobenzene and $NH_3$ (Ref. U.S. Pat. 3,057,922) or by catalytic hydrogenation of 1-chloro-4-nitrobenzene (Ref. U.S. Pat. 3,145,231).

The catalytic liquid phase chlorination of 1,2-dichlorobenzene (1,2-DCB) is investigated over a number of zeolite catalysts using chlorine as chlorinating agent. Both K-L and K-beta are effective catalysts for the selective conversion of 1,2-DCB to 1,2,4-trichlorobenzene (1,2,4-TCB). (*Appl. Catal. A*, 1997, 162, 201). A catalyst was prepared by loading 3.0% $Cu(NO_3)_2.3H_2O$ and 2.0% NaCl into zeolite KL by grinding and calcined at 550° for 6 h. Liquid-phase chlorination of PhCl in the presence of this catalyst gave a 92.5% conversion to $C_6H_4Cl_2$ with para-ortho ratio 12.2:1 (Ref. PCT Int. Appl. WO 9718893 A1 29 May 1997, 20 pp).

Chlorination of chlorobenzene in the presence of $FeCl_3$ and Ph 10H-phenothiazine-10-carboxylate at 50° C. in the dark for 7 h gave a product mixture containing o-dichlorobenzene, m-dichlorobenzene, p-dichlorobenzene and trichlorobenzene (Ref. PCT Int. Appl. WO 9743041 A1 20 Nov. 1997, 36 pp). The synthesis of 2,4-dichlorotoluene (2,4-DCT) was studied at 368 K and at atmospheric pressure using zeolite catalysts and the conventional catalyst, $FeCl_3$, in the liquid phase chlorination of 4-chlorotoluene (4-CT) with gaseous chlorine ($Cl_2$ flow =0.09 mol/h) and catalyst conc. of 3.78 g/mol 4-CT. Zeolite K-L catalyzes 4-CT selectively to 2,4-DCT and is superior to the other zeolites and $FeCl_3$ in terms of selectivity (Ref (1) *J. Mol. Catal. A: Chem.* 1997, 127, 101; (2) *Stud Sur Sci. Catal.* 1998, 113, 419). A solid-liquid biphasic system (dichloromethane and neutral alumina) has been tested for the aromatic chlorination of various alkyl aryl ethers using a reagent combination of sodium chlorite and manganese(III) acetylacetonate catalyst. Efficient incorporation of a chlorine atom into the benzene ring with high para selectivity results. This catalytic system is also applicable to the regiocontrolled chlorination of polyether substrates. (Ref *J. Chem. Soc., Perkin Trans.* 1 1997, 3081). Loading of zeolite NaZSM-5 with benzene and chlorine from the gas phase at −100° C. resulted in spontaneous reaction to form chlorobenzene and 1,4-dichlorobenzene as the sole products. Thermal reaction at elevated temp. (up to 0° C.) accelerates the rates toward these products and yields, in addition, some 1,3-dichlorobenzene and a small (<3%) amount of 1,2-dichlorobenzene (Ref. *J. Phys. Chem. B*, 1998, 102, 7106).

tert-Butyl hypochlorite is an excellent aromatic ring chlorination agent, under mild conditions, without any catalyst, for acetanilide. High regioselectivity is observed, the product being, nearly exclusively, para-chloroacetanilide (Ref. *Synth. Commun.* 1998, 28, 1891). Aromatic compounds were chlorinated in the presence of catalytic 4-$PSC_6H_4$ $(CH_2)_xSR_1SR_2$ or $X_1R_3(SR_4SR_3)_ySR_4X_2$ [PS=polymeric backbone preferably selected from polystyrene or polysiloxane, e.g. polyalkylsiloxane or polyalkylarylsiloxane; x=0–12; $R_1$–$R_4$=(substituted) alkyl, alkanediyl, (substituted) alkaryl, aralkyl, aryl; $X_1$, $X_2$=halo, SH, dialkylsulfonium halide, alkylaryl, aralkyl, (substituted) aryl; y £10000] and optionally in the presence of Lewis acid cocatalysts. Thus, m-cresol and catalytic $AlCl_3$ and 4-$PSC_6HCH_2S(CH_2)_4SBu$ (PS=polystyrene) were treated with $SO_2Cl_2$ to give 6.4 mol % o-chloro-m-cresol and 81 mol % p-chloro-m-cresol (Ref. Eur. Pat. Appl. EP 866048, September 1998, 58249404u, 17 pp). The active quinonoid position of various naphthoquinones is chlorinated by metal (II) chloride (CuCl$_2$/HgCl$_2$) and iodine in acetic acid in a single step reaction with excellent yields (Ref. *Synth. Commun.* 1998, 28, 1123).

The reaction of alkyl phenyl ethers with sodium chlorite in dichloromethane in the presence of a (salen) manganese (III) complex and alumina preloaded with a small amount. of water afforded monochlorination products with unusually high para selectivities under mild conditions. The NaClO$_2$-based biphasic system can also be successfully used for the regioselective monochlorination of substituted anisoles and polmethyoxybenzenes (Ref *Can. J. Chem.* 1997, 75, 1905).

Tert-Butyl hypochlorite/HNa faujasite X in acetonitrile represents an efficient and highly regioselective system for mono-chlorination of a wide range of mono- and di-substituted aromatic substrates in mild conditions. Partially protonated faujasite X is far superior to amorphous silicas and to other zeolites in terms of efficiency and regioselectivity (Ref. *Green Chem.* 1999, 1, 83). Aromatic compounds are chlorinated in the vapor phase in the presence of a catalyst on a natural solid acid selected from bentonite, oxidized white clay, silica-alumina, celite and kaolin at 30–300° C.; using solid acids as catalyst. (Ref Repub. Korea KR 9602193 B 1,13 Feb. 1996).

p-Chloroethylbenzene was prepared by reaction of ethylbenzene with Cl$_2$ in 1,2-dichloropropane in the presence of L-type zeolites. Thus, reaction of ethylbenzene with Cl$_2$ in 1,2-dichloropropane in the presence of L-type zeolite at 80° for 3.5 h gave p-chloroethylbenzene with 80.8% selectivity and 95.0% conversion rate for ethylbenzene (Ref. JP 2000128811 A2, 9 May 2000, 3 pp). The chloro compounds were prepared by regioselective chlorination of aromatic compounds with Lewis acid catalysts in the presence of NO$_2$-containing aromatic compounds. Toluene was chlorinated with Cl in the presence of SbCl$_5$ and o-NO$_2$C$_6$H$_4$Me at 50° C. for 1 h to give 41.1% oClC$_6$H$_4$Me and 15.2% p-ClC$_6$H$_4$Me (Ref. JP 2001151707 A2, 5 June 2001, 7 pp). Monosubstituted benzenes were halogenated by treating them with halogens in liquid phase in the presence of zeolites and aliphatic nitro compounds. A mixture of PhCH$_2$CH$_2$Br, HSZ 500KOA (L-zeolite), and MeNO$_3$ was bubbled with Cl at 30° C. for 2 h and the reaction mixture was kept at 30° C. for 1 h to give p-ClC$_6$H$_4$CH$_2$CH$_2$Br and o-ClC$_6$H$_4$CH$_2$CH$_2$Br with selectivities 70.6 and 24.5%, respectively, at conversion 18.4% (Ref JP 2001072620 A2, 21 March 2001, 5 pp).

p-C$_6$H$_4$Cl$_2$ (p-I) is prepared by liquid-phase chlorination of C$_6$H$_6$ and/or PhCl in the presence of N-substitutedphthalimides and Lewis acids. PhCl containing FeCl$_3$ and phthalimide and Cl$_2$ were continuously fed to a reactor at 60° C. for 6 h to give a reaction mixture containing PhCl 61.63, p-I 28.70, o-I 9.47, m-I 0.07, and C$_6$H$_3$Cl$_3$ 0.08% at Cl conversion 99.91% (Ref. JP 2002114719 A2, 16 April 2002, 5 pp).

Although, all the methods mentioned above in the prior art are known to be useful for the chlorination of aromatic substrates, they suffer from the following drawbacks:

1. Many of the reagents mentioned above lead to radical chlorination resulting in substitution in the side chain of arenes rather than on the ring, under the reaction conditions of higher temperature or irradiation with ultra violet light.
2. As mentioned in prior art o-chlorination of phenol with SO$_2$Cl$_2$ in the presence of amines gives small amounts of polychlorophenols.
3. The heterogeneous catalytic route involving the use of acidic zeolite ZF520 as catalyst also suffers from disadvantages like side chain chlorination, use of inhibitor, etc.
4. Activated aromatics have been found to undergo polychlorinations rather than monochlorination resulting in the mixture of isomers, which are difficult to separate.
5. In most of the methods mentioned in the prior art chlorine is used as the halogen source, which is poisonous, corrosive and difficult to handle.
6. Some of the methods mentioned in prior art make use of metal salts in stochiometric amount, which generates lot of solid waste during the reaction.
7. Some of the methods described in prior art involve very high temperature reactions, which are difficult to handle, and often leads to variety of side products.

OBJECTS OF THE INVENTION

The main object of the invention is to provide a process for the chlorination of alkanes, alkenes and arenes which overcomes the drawbacks of the prior art identified above.

It is another object of the invention to use hypervalent iodine as a very high regioselective halogenation catalyst in the chlorination of alkanes, alkenes and arenes.

It is a further object of the invention to use sodium chloride as a chlorine source thereby rendering the process environmentally safe and economical due to the sources wide abundance.

It is another object of the invention to provide a process for the chlorination of alkanes, alkenes and arenes wherein quantitative conversions are obtained even for less active substrates such as 2-nitroanisole and acetophenone.

It is a further object of the invention to provide a process for the chlorination of alkanes, alkenes and arenes wherein high temperatures are not required thereby resulting in energy savings and rendering the process more economical.

SUMMARY OF THE INVENTION

Accordingly, the present invention provides a process for regiospecific chlorination of an aromatic or aliphatic compound with a chlorine source comprising a metal chloride and other than Cl$_2$ and SO$_2$Cl$_2$ in presence of hypervalent iodine catalyst and in acidic medium.

In one embodiment of the invention, the aliphatic compound is selected from alkanes and alkenes.

In another embodiment of the invention, the aromatic compound is selected from arenes.

In yet another embodiment of the invention, the reaction is carried out at a temperature in the range of 70–80° C. for a time period in the range of 4–24 h.

In yet another embodiment of the invention, the reaction is terminated by bringing the reaction mixture to ambient temperature followed by extracting and purifying the product.

In another embodiment of the invention, the extraction is done by solvent extraction.

In another embodiment of the invention, the chlorine source is sodium chloride.

In another embodiment of the invention, the hypervalent iodine (iodine valency ranging from +3 to +7) catalyst is selected from the group consisting of NaIO$_4$ and PhI(Oac)$_2$, preferably NaIO$_4$ in liquid phase.

In another embodiment of the invention, the reactants are dissolved in a solvent selected from the group consisting of DME, dioxane, H$_2$O, acetonitrile, chloroform, ethylene dichloride, and any combination thereof.

In a further embodiment of the invention, the solvent comprises a combination of CH$_3$CN: water (2:1).

In another embodiment of the invention, the pH of the reaction mixture is brought to a range of 2–6 by addition of 10–20% mineral acid solution.

DETAILED DESCRIPTION OF THE INVENTION

The present invention provides a new process for the synthesis of aryl and alkyl chlorides. In addition, the process operates under milder conditions providing facile isolation of products (Scheme 1).

Scheme 1: NaIO$_4$-catalyzed chlorination of C—H bond

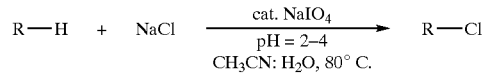

R = Alkyl, aryl, etc.

In one aspect, a process according to the present invention for the preparation of aryl or alkyl chlorides comprises reaction of corresponding alkanes or arenes of formula R-H and metal chloride in presence of hypervalent iodine as a catalyst in acidic medium.

The present invention therefore provides a new catalytic process for highly regiospecific chlorination of alkanes, alkenes and arenes which comprises treating the acidic solution of alkanes, alkenes and arenas in an organic solvent with a chlorine source and a hypervalent iodine catalyst at a temperature ranging between 70–80° C. for a period of 4–24 h, then terminating the reaction by bringing the reaction mixture to room temperature, extracting the product by conventional methods like solvent extraction and purifying by conventional methods to obtain the product. The hypervalent iodine catalyst may be NaIO$_4$ and the chlorine source for chlorination may be sodium chloride. The solvent used for dissolving substrates may be acetonitrile, methanol. The pH of the reaction mixture may be in the range of 2–6 adjusted by addition of 10–20% mineral acid solution.

The process of the present invention is described herein with reference to illustrative and non-limiting examples.

Example 1

Preparation of chlorobenzene

Benzene (1 mmol) was treated with sodium chloride (1.2 mmol) in acetonitrile: water (2:1, 6 ml). 20% Sulfuric acid (5 ml) and sodium periodate (20 mol %) was added to the reaction mixture. The mixture was heated at 80° C. under inert atmosphere for 6 h. The product was purified by column chromatography to give chlorobenzene (33%).

Example 2

Preparation of 2,4-dichlorotoluene

Toluene (1 mmol) was treated with sodium chloride (1:2 mmol) in acetonitrile: water (2:1, 6 ml). 20% Sulfuric acid (5 ml) and sodium periodate (20 mol %) was added to the reaction mixture. The mixture was heated at 80° C. under inert atmosphere for 6 h. The product was purified by column chromatography to give 2,4-dichlorotoluene (15%).

Example 3

Preparation of 4-chloroanisole

Anisole (1 mmol) was treated with sodium chloride (1.2 mmol) in acetonitrile: water (2:1, 6 ml). 20% Sulfuric acid (5 ml) and sodium periodate (20 mol %) was added to reaction mixture. The mixture was heated at 80° C. under inert atmosphere for 4 h. The product was purified by column chromatography to give 4-chloroanosole (25%) and 2-chloroanisole (2%).

Example 4

Preparation of 2-nitro-4-chloroanisole

2-Nitroanisole (1 mmol) was treated with sodium chloride (1.2 mmol) in acetonitrile: water (2:1, 6 ml). 20% Sulfuric acid (5 ml) and sodium periodate (20 mol %) was added to the reaction mixture. The mixture was heated at 80° C. under inert atmosphere for 4 h. The product was purified by column chromatography to give 2-nitro-4-chloroanosole (55%).

Example 5

Preparation of 1,4-dichlorobenzene

Chlorobenzene (1 mmol) was treated with sodium chloride (1.2 mmol) in acetonitrile: water (2:1, 6 ml). 20% Sulfuric acid (5 ml) and sodium periodate (20 mol %) was added to the reaction mixture. The mixture was heated at 80° C. under inert atmosphere for 6 h. The product was purified by column chromatography to give 1,4-dichlorobenzene (8%).

Example 6

Preparation of chloromesitylene

Mesitylene (1 mmol) was treated with sodium chloride (1.2 mmol) in acetonitrile: water (2:1, 6 ml). 20% Sulfuric acid (5 ml) and sodium periodate (20 mol %) was added to the reaction mixture. The mixture was heated at 80° C. under inert atmosphere for 6 h. The product was purified by column chromatography to give chloromesitylene (40%).

Example 7

Preparation of α-chloroacetophenone

Acetophenone (1 mmol) was treated with sodium chloride (1.2 mmol) in acetonitrile: water (2:1, 6 ml). 20% Sulfuric acid (5 ml) and sodium periodate (20 mol %) was added to the reaction mixture. The mixture was heated at 80° C. under inert atmosphere for 6 h. The product was purified by column chromatography to give α-chloroacetophenone (55%).

Example 8

Preparation of α-chloro-4-chloroacetophenone

4-Chloroacetophenone (1 mmol) was treated with sodium chloride (1.2 mmol) in acetonitrile: water (2:1, 6 ml). 20% Sulfuric acid (5 ml) and sodium periodate (20 mol %) was added to reaction mixture. Mixture was heated at 70° C. under inert atmosphere for 6h. Product was purified by column chromatography to give α-chloro4-chloroacetophenone (57%).

Example 9

Preparation of monochlorocyclohexane

Cyclohexane (10 ml) was treated with sodium chloride (1.2 mmol) in acetonitrile: water (2:1, 6 ml). 20% Sulfuric acid (5 ml) and sodium periodate (20 mol %) was added to reaction mixture. Mixture was heated at 80° C. under inert atmosphere for 14 h. Product was purified by column chromatography to give monochlorocyclohexane (25% based on NaCl).

Example 10

Preparation or monochlorocycloctane

Cyclooctane (10ml) was treated with sodium chloride (1.2 mmol) in acetonitrile: water (2:1, 6 ml). 20% Sulfuric acid (5 ml) and sodium periodate (20 mol %) was added to reaction mixture. Mixture was heated at 80° C. under inert atmosphere for 18 h. Product was purified by column chromatography to give monochlorocycloctane (20% based on NaCl used).

Example 11

Preparation of 1-chlorohexane n-Hexane (10 ml) was treated with sodium chloride (1.2 mmol) in acetonitrile: water (2:1, 6 ml). 20% Sulfuric acid (5 ml) and sodium periodate (20 mol %) was added to reaction mixture. The mixture was heated at 80° C. under inert atmosphere for 24 h. The product was purified by column chromatography to give 1-chlorohexane (24% based on NaCl used).

Example 12

Preparation of 1-phenyl-2-chloroethanol

Styrene (1 mmol) was treated with sodium chloride (1.2 mmol) in acetonitrile: water (2:1, 6 ml). 20% Sulfuric acid (5 ml) and sodium periodate (20 mol %) was added to the reaction mixture. The mixture was heated at 70° C. under inert atmosphere for 18 h. The product was purified by column chromatography to give 1-phenyl-2-chloroethanol (95%).

TABLE 1

$NaIO_4$ catalyzed chlorination of alkanes, alkenes and arenes using sodium chloride as chlorine source.

| Ex. No. | Substrate | Time (h) | Conversion[a] (%) | Selectivity[b] (%) | Others (%) |
|---|---|---|---|---|---|
| 1. | Benzene | 6 | 35 | 94 | 6[c] |
| 2. | Toluene | 6 | 16 | 94 | 6[d] |
| 3. | Anisole | 4 | 27 | 93 | 7 |
| 4. | 2-Nitroanisole | 4 | 60 | 100 | — |
| 5. | Chlorobenzene | 6 | 10 | 80 | 20[e] |
| 6. | Mesitylene | 6 | 43 | 100 | — |
| 7. | Acetophenone | 6 | 58 | 100 | — |
| 8. | p-Chloroacetophenone | 6 | 60 | 100 | — |
| 9. | Cyclohexane | 14 | 30 | 83 | 17[f] |
| 10. | Cyclooctane | 18 | 32 | 63 | 37[f] |
| 11. | n-Hexane | 24 | 40 | 60 | 40[g] |
| 12. | Styrene | 18 | 95 | 100[h] | — |

[a]determined by GC with capillary column;
[b]for specific product, see examples;
[c]1,4-dichlorobenzene;
[d]2,4-dichlorobenzylchloride;
[e]1,2-dichlorobenzene;
[f]polychloro compounds;
[g]2-chlorohexane and 3-chlorohexane;
[h]1-phenyl-2-chloroethanol.

The advantages of the present invention are:
1. This is the first disclosure of the use of hypervalent iodine as a very high regioselective halogenation catalyst.
2. Sodium chloride (NaCl) was used as a chlorine source, which is abundant, safe, non-corrosive and cheaply available.
3. Only mono chlorination takes place even with highly activated aromatic substrates.
4. No or very less side chain chlorination was observed in case of alkyl substituted aromatic compounds like toluene.
5. Quantitative conversions are obtained even in case of less activated substrates such as 2-nitroanisole and acetophenone, with sodium chloride as a chlorine source.
6. Anhydrous condition or very high temperature is not required for effective conversion. Process works in a wide range of temperatures varying from 0 to 200° C. Particularly high conversions are observed in the temperature range of 60–80° C.
7. Aqueous medium can be used to carry out the reaction without affecting the conversion and selectivity.
8. A variety of aromatic compounds both activated (with substituents such as Ome, alkyl, halo, OH, $NH_2$, NHR, etc.) and non-activated (with substituents such as $COCH_3$, COOH, $NO_2$, CN, $CF_3$, CHO, etc.) are chlorinated successfully with good conversions and excellent selectivity. Alkanes such as cyclohexane, n-hexane and cyclooctane are also monochlorinated with good selectivity. Alkenes such as styrene, stilbene, cyclohexene, methyl cinnamate, chalcone, or substituted there of, etc. are chlorinated to afford the corresponding 1,2-chloroalcohols in high yields.

We claim:

1. A process for regiospecific chlorination of an aromatic or aliphatic compound with a chlorine source comprising a metal chloride other than $Cl_2$ or $SO_2Cl_2$ in presence of hypervalent iodine catalyst and in acidic medium.

2. A process as in claim 1 wherein the aliphatic compound is selected from alkanes and alkenes.

3. A process as in claim 1 wherein the aromatic compound is selected from arenes.

4. A process as in claim 1 wherein the reaction is carried out at a temperature in the range of 70–80° C. for a time period in the range of 4–24 h.

5. A process as in claim 1 wherein the reaction is terminated by bringing the reaction mixture to ambient temperature followed by extracting and purifying the product.

6. A process as in claim 5 wherein the extraction is done by solvent extraction.

7. A process as in claim 1 wherein the chlorine source is sodium chloride.

8. A process as claim 1 wherein the hypervalent iodine (iodine valency ranging from +3 to +7) catalyst is selected from the group consisting of $NaIO_4$ and $PhI(Oac)_2$, preferably $NaIO_4$ in liquid phase.

9. A process as in claim 1 wherein the reactants are dissolved in a solvent selected from the group consisting of DMF, dioxane, $H_2O$, acetonitrile, chloroform, ethylene dichloride, and any combination thereof.

10. A process as in claim 9 wherein the solvent comprises a combination of $CH_3CN$: water (2:1).

11. A process as in claim 1 wherein the pH of the reaction mixture is brought to a range of 2–6 by addition of 10–20% mineral acid solution.

* * * * *